(12) United States Patent
Fitch et al.

(10) Patent No.: US 8,840,705 B2
(45) Date of Patent: Sep. 23, 2014

(54) METHODS FOR THE OZONOLYSIS OF ORGANIC COMPOUNDS

(75) Inventors: Frank R. Fitch, Bedminster, NJ (US); Naresh J. Suchak, Glen Rock, NJ (US)

(73) Assignee: Linde Aktiengesellschaft, Munich (DE)

( * ) Notice: Subject to any disclaimer, the term of this patent is extended or adjusted under 35 U.S.C. 154(b) by 148 days.

(21) Appl. No.: 13/539,783

(22) Filed: Jul. 2, 2012

(65) Prior Publication Data

US 2013/0177497 A1 Jul. 11, 2013

Related U.S. Application Data

(60) Provisional application No. 61/505,162, filed on Jul. 7, 2011.

(51) Int. Cl.
| | | |
|---|---|---|
| *B01D 53/047* | (2006.01) | |
| *C02F 1/78* | (2006.01) | |
| *C01B 13/10* | (2006.01) | |
| *B01D 53/22* | (2006.01) | |
| *C07C 45/40* | (2006.01) | |
| *C07C 51/34* | (2006.01) | |

(52) U.S. Cl.
CPC . *C01B 13/10* (2013.01); *C02F 1/78* (2013.01); *B01D 53/22* (2013.01); *C07C 45/40* (2013.01); *C07C 51/34* (2013.01); *B01D 53/047* (2013.01); *B01D 2253/106* (2013.01); *B01D 2253/108* (2013.01); *B01D 2256/14* (2013.01); *B01D 2257/104* (2013.01)
USPC ........ 95/138; 210/760; 423/581; 422/186.08; 422/186.12

(58) Field of Classification Search
CPC ................. B01D 53/047; B01D 53/22; B01D 2253/106; B01D 2253/108; B01D 2256/14; B01D 2257/104; C01B 13/10; C07C 45/40; C07C 51/34; C02F 1/78
USPC ......... 210/192, 760; 96/4, 108; 95/45, 54, 90, 95/96, 138; 422/186.07, 186.08, 186.12; 423/581

See application file for complete search history.

(56) References Cited

U.S. PATENT DOCUMENTS

| | | | | |
|---|---|---|---|---|
| 2,872,397 | A * | 2/1959 | Kiffer | 204/176 |
| 3,505,213 | A | 4/1970 | Anthony et al. | |
| 3,856,671 | A * | 12/1974 | Lee et al. | 210/760 |
| 3,963,625 | A * | 6/1976 | Lowther | 422/186.11 |
| 4,940,808 | A | 7/1990 | Schulz et al. | |
| 5,520,887 | A * | 5/1996 | Shimizu et al. | 422/186.08 |
| 6,030,598 | A * | 2/2000 | Topham et al. | 423/581 |
| 6,193,852 | B1 | 2/2001 | Caracciolo et al. | |
| 6,197,091 | B1 | 3/2001 | Ji et al. | |
| 6,916,359 | B2 * | 7/2005 | Jain | 95/99 |
| 7,766,995 | B2 | 8/2010 | Suchak et al. | |
| 8,029,603 | B2 * | 10/2011 | Weist, Jr. | 95/96 |

FOREIGN PATENT DOCUMENTS

JP 53-039993 * 4/1978

* cited by examiner

*Primary Examiner* — Frank Lawrence
(74) *Attorney, Agent, or Firm* — Philip H. Von Neida

(57) ABSTRACT

A method for producing ozone for use in ozonolysis reactions. Oxygen is separated from the mixture of ozone and oxygen from an ozone generation unit and is fed back to the oxygen feed to the generation unit. Nitrogen is fed to the ozone separation unit and the mixture of nitrogen and ozone is fed to the ozonation reactor where the ozone will react with organic compounds to produce desired end products.

8 Claims, 2 Drawing Sheets

METHODS FOR THE OZONOLYSIS OF ORGANIC COMPOUNDS

CROSS REFERENCE TO RELATED APPLICATIONS

The present application claims priority from U.S. provisional patent application Ser. No. 61/505,162, filed Jul. 7, 2011.

BACKGROUND OF THE INVENTION

Alkenes can be oxidized with ozone to form alcohols, aldehydes/ketones or carboxylic acids. In a typical procedure, ozone is bubbled through a solution of the alkene in methanol at −78° C. A reagent is then added to convert the intermediate ozonide to a carbonyl derivative. Reductive work-up conditions are far more commonly used than oxidative conditions. The use of triphenylphosphine, thiourea, zinc dust or dimethyl sulfide produces aldehydes or ketones while the use of sodium borohydride produces alcohols. The use of hydrogen peroxide produces carboxylic acids.

Other functional groups, such as benzyl ethers, can also be oxidized by ozone. Dichloromethane is often used as a 1:1 cosolvent to facilitate timely cleavage of the ozonide. Azelaic acid and pelargonic acids are produced from ozonolysis of oleic acid on an industrial scale.

Ozonolysis of alkynes generally gives an acid anhydride or diketone product, not complete fragmentation as for alkenes. A reducing agent is not needed for these reactions. If the reaction is performed in the presence of water, the anhydride hydrolyzes to give two carboxylic acids.

Ozone is an unstable gas and therefore is produced using ozone generators on-site on-demand. Ozone generators are safe industrial components that are highly reliable and provide long service life. Ozone generators are commonly used in drinking water, waste water, pulp bleaching and swimming pool water treatment applications as well as in fine chemical ozonolysis and other reactions.

An ozone generator vessel is similar to a shell and tube heat exchanger. Ozone is generated as oxygen from clean dry air, oxygen enriched air or pure oxygen is passed through the water-cooled tubes of the heat exchanger. Inside the tubes, there is a dielectric containing an electrode connected to an electrical power source. When an electrical current passes through the dielectric, a corona discharge is produced. Di-oxygen ($O_2$) molecules flowing through corona discharge are dissociated freeing oxygen atoms, which quickly combine with available oxygen molecules to form ozone ($O_3$) molecules. The dilute ozone containing gas stream generated within the stainless steel or glass generator vessel is generally used directly in the industrial application.

When air is used as the feed gas to the ozone generator, then ozone concentrations up to around 5% (typically about 2.5% by volume) can be obtained, whereas when oxygen of greater than 90% purity is used, ozone concentrations up to around 15% (typically about 10% by volume) can be obtained. Generally, the economics favor the use of oxygen rather than air for ozone generation, as both capital and power costs are further reduced and more than offset the costs of oxygen required, despite the fact that typically 90% of the oxygen fed to the ozone generator passes unreacted through the ozone generator.

As ozone has a finite lifetime at ambient pressures and temperatures, it is produced on demand in quantities matched to the instantaneous requirements of the process requiring ozone.

Several approaches have been proposed to increase the utilization level of oxygen in oxygen-based ozone generation applications. Several recycle processes recycle oxygen after the ozone application. The oxygen purification process needs to be customized for impurities generated in the industrial application and can be quite expensive and potentially unsafe.

Other approaches include an alternative oxygen recycle scheme according to U.S. Pat. No. 6,916,359 B2 of common assignment herewith in which a pressure swing adsorption (PSA) unit is used to recycle 65 to 70% of the unreacted oxygen and ozone is adsorbed from the ozone-oxygen mixture on selected adsorbents prior to the ozone application. Un-adsorbed oxygen is recycled and ozone is then desorbed using clean dry air (CDA) or waste gas into the customer ozone application. This recycle process is independent of the nature of the ozone application, is easy to design and control and eliminates oxygen purification and safety-related issues.

This approach was further extended in U.S. Pat. No. 7,766,995 B2 of even assignment herewith from waste water applications to more general industrial ozone applications.

In most industrial applications such as water treatment or nitrogen oxides abatement, the presence of excess oxygen in the ozone stream does not cause significant process or safety issues and hence oxygen-based ozone generation is widely used as this leads to lower costs than air-based ozone generation.

However, in the case of ozonation of organics, the safety implication of the replacement of air-based ozone generation with oxygen-based ozone generation must be carefully considered. In particular, organic solvents that may not be flammable in air may form explosive mixtures in pure oxygen, especially in the presence of excess ozone. Methanol is clearly flammable in air, let alone oxygen, with a flash point in air of 54° C. The common co-solvent used with methanol in ozonolysis, dichloromethane (methylene (di)chloride) is often mistakenly thought not to be flammable in air. Although it will not burn at ambient temperatures and pressures, it will form explosive mixtures in air at temperatures greater than about 100° C. and has a flash point in pure oxygen of −7.1° C.

A standard approach for reducing oxygen concentrations to safe levels in organic reaction vessels is to flush the headspace with large quantities of nitrogen. This can be relatively expensive and can lead to the loss by evaporation of significant quantities of volatile species such as solvents. Accordingly, an inherently safe method for introducing ozone into ozonolysis reaction systems, in which the cost advantages of oxygen-based ozone generation can be realized without introducing elevated levels of oxygen into the headspace of the reactor, is desirable.

SUMMARY OF THE INVENTION

In a first embodiment of the invention, there is disclosed a method for generating ozone for use in the ozonolysis of organic compounds comprising the steps of:
a) feeding liquid oxygen to a heat exchanger thereby forming gaseous oxygen;
b) feeding gaseous oxygen to an ozone generator;
c) feeding a mixture of ozone and oxygen to an ozone separation unit;
d) feeding liquid nitrogen to a heat exchanger thereby forming gaseous nitrogen and feeding the gaseous nitrogen to the ozone separation unit; and
e) returning oxygen separated from the mixture of ozone and oxygen to the gaseous feed of oxygen and feeding a mixture of ozone and nitrogen to an ozonation reactor.

In a further embodiment of the invention, there is disclosed a method for generating ozone for use in the ozonolysis of organic compounds comprising the steps of:
a) feeding liquid oxygen to a heat exchanger thereby forming gaseous oxygen;
b) feeding gaseous oxygen to an ozone generator;
c) feeding a mixture of ozone and oxygen to an ozone separation unit, whereby oxygen is separated and is discharged from the ozone separation unit;
d) feeding liquid nitrogen to a heat exchanger thereby forming gaseous nitrogen and feeding the gaseous nitrogen to the ozone separation unit; and
e) feeding a mixture of ozone and nitrogen to an ozonation reactor.

In a further embodiment of the invention, there is disclosed a method for generating ozone for use in the ozonolysis of organic compounds comprising the steps of:
a) feeding liquid oxygen to a heat exchanger thereby forming gaseous oxygen;
b) feeding gaseous oxygen to an ozone generator;
c) feeding a mixture of ozone and oxygen to an ozone separation unit;
d) feeding liquid nitrogen to a temperature control unit whereby the liquid nitrogen is heated and becomes gaseous;
e) feeding the gaseous nitrogen to the ozone separation unit;
f) feeding a mixture of ozone and nitrogen to an ozonation reactor; and
g) transferring cooling from the temperature control unit to a cooling jacket surrounding the ozonation reactor.

An oxygen based ozone generation system is used. In this embodiment, bulk oxygen is utilized, although other means of oxygen supply such as cryogenic oxygen generators, pipelines, vacuum pressure swing adsorption (VPSA) units, pressure swing adsorption (PSA) units, membrane systems and other means to generate oxygen may also be employed.

The ozone/oxygen mixture is separated using an oxygen to ozone unit (OOU)-style PSA system. A high purity adsorbent material that does not significantly decompose adsorbed ozone, such as selected silica gel or high silica zeolite adsorbents will concentrate the ozone allowing 50 to 70 plus % of the unreacted oxygen to be recycled back to the ozone generator. Alternatively, a membrane-based separation system is also envisaged. Pure nitrogen is utilized to flush the ozone into the ozonation reactor. This nitrogen may come from a bulk nitrogen supply system as illustrated in the FIG. 1, or from other means such as a nitrogen PSA. Residual oxygen levels, resulting from flushing of the dead space in the adsorber vessel are reduced to safe levels, lower indeed than those found in standard air-based ozone generation systems. An inherently safe ozonolysis process may be operated and the cost of ozone generation can be further reduced as most of the unreacted oxygen is recycled and not wasted.

The ozonolysis could be performed on a variety of organic compounds, intermediates and the like, such as alkenes to form alcohols, aldehydes/ketones or carboxylic acids. Other functional groups, such as benzyl ethers, can also be oxidized by ozone. Dichloromethane is often used as a 1:1 cosolvent to facilitate timely cleavage of the ozonide. Azelaic acid and pelargonic acids are produced from ozonolysis of oleic acid. Alkynes can also be subjected to ozonolysis to form acid anhydride or diketone products.

In another embodiment as shown in FIG. 2, oxygen separated from the ozone/oxygen mixture is not recycled back to ozone generator but exhausted to the atmosphere or gainfully utilized in oxygen application elsewhere such as aerobic waste oxidation eliminating need for recycle booster blower (or compressor).

In a different embodiment as shown in FIG. 3, indirect cryogenic cooling is used to keep the temperature of the ozonolysis reactor efficiently at $-40°$ C. to $-80°$ C. $+/-1°$ C. as required by the reaction such as those used in the Linde CUMULUS™ system. The waste pure nitrogen resulting from the cryo-cooling can be used to flush the ozone into the system, further reducing the cost of the improved process of the invention. In this instance, some utilization of the waste cooling contained in the gaseous nitrogen (GAN) stream may also be utilized further improving the overall efficiency of the process.

DETAILED DESCRIPTION OF THE INVENTION

Figure 1:
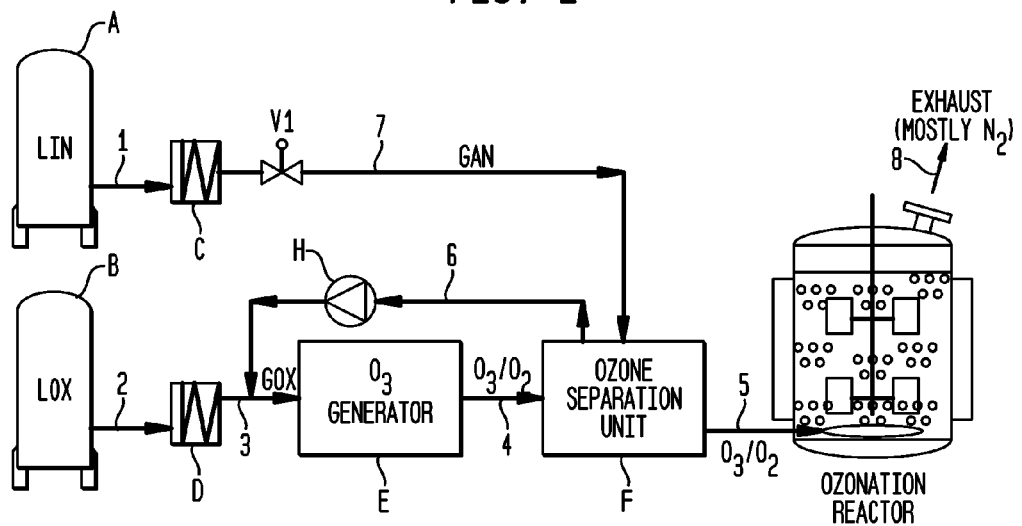
FIG. 1 is a schematic of the process for the ozonation of organics per the invention.

Turning to FIG. 1, a schematic representation of a process according to the invention is presented. Ozone is produced for use in an ozonolysis reaction in an ozonation reactor. Liquid nitrogen is stored in storage tank A and fed through line 1 to a heat exchanger C. The liquid nitrogen will be warmed and enters the gaseous state in heat exchanger C. When valve V1 is opened, the gaseous nitrogen will be fed through line 7 into the ozone separation unit F.

Liquid oxygen is stored in storage tank B. Liquid oxygen is fed through line 2 to heat exchanger D where its temperature will be raised and it will become gaseous. The gaseous oxygen is fed through line 3 to an ozone generator E where it will be used to produce ozone. A mixture of oxygen and ozone will leave ozone generator E through line 4 to an ozone separation unit F. In this unit, ozone and oxygen are separated by conventional means such as an adsorption process or through membranes and the separated oxygen is fed back through line 6 through a booster blower or compressor (H) where it will rejoin the gaseous oxygen in line 3 for re-entry into the ozone generator E.

The ozone separation unit F will separate the ozone and allow it to mix with the gaseous nitrogen from line 7 and this mixture is fed through line 5 to an ozonation reactor G where the ozone will react with organic compounds, intermediates, or other fine chemicals to form desired end products. The nitrogen that is present in the ozonation reactor G will be released into the exhaust duct or atmosphere through line 8.

In an alternative embodiment, the nitrogen from line 7 may be employed to provide cooling to the ozonation reactor.

Figure 2:
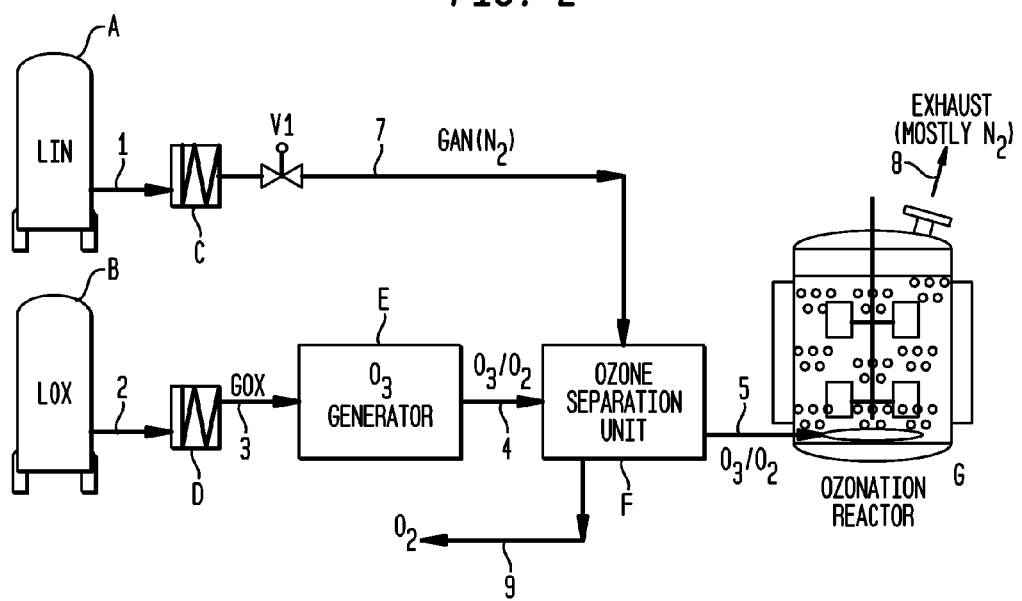
FIG. 2 is a schematic of the process for the ozonation of organics per the invention without oxygen recycle.

In FIG. 2, the same numbering will apply as in FIG. 1 except that line 6 has been removed from the description of FIG. 2. The oxygen that was recycled through line 6 and booster blower or compressor H has been removed and is replaced by line 9 to signify that the oxygen separated in the ozone separation unit F is released into the atmosphere, fed to water or wastewater or fed to another unit operation at the site where the organic compounds undergo ozonolysis.

Figure 3:
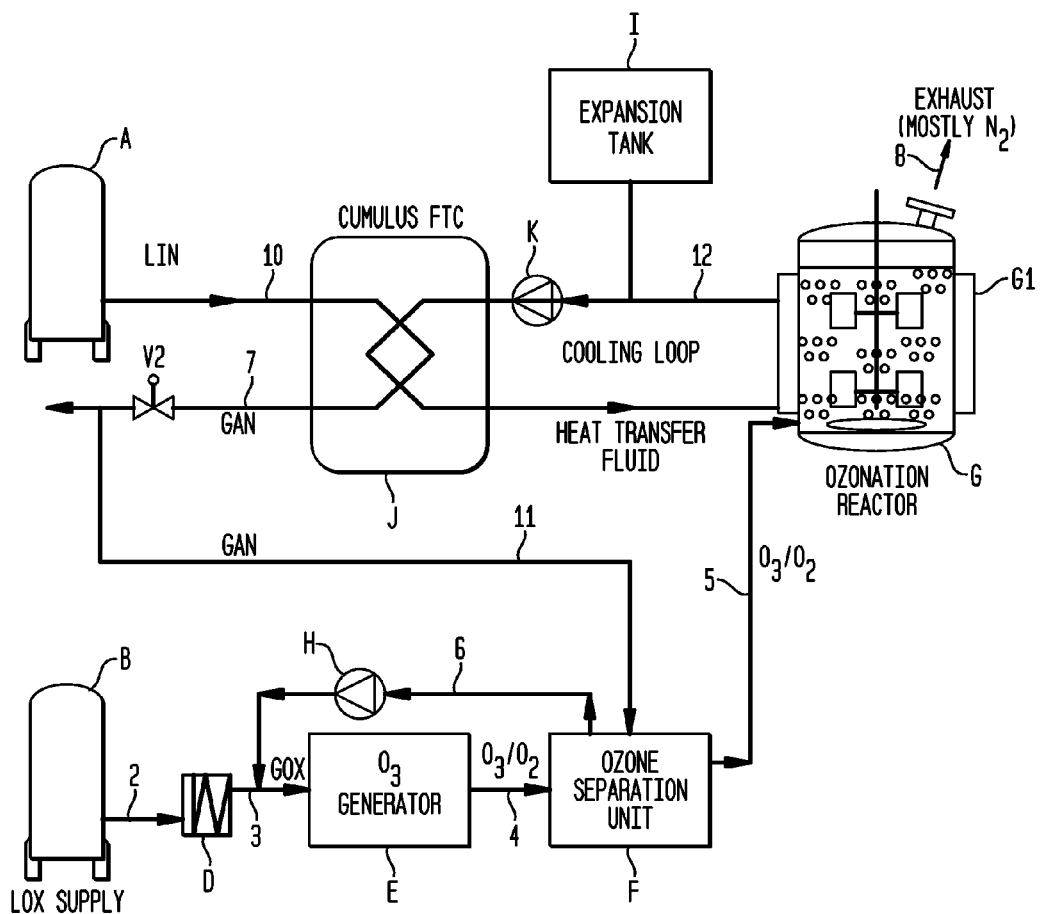
FIG. 3 is a schematic of the process for the ozonation of organics per the invention wherein indirect cooling is applied to the ozonation reactor.

In FIG. 3, similar numbering is used to describe the process of supplying liquid oxygen from storage tank B to the ozone separation unit F as in FIG. 1. The process whereby nitrogen is added to the ozone separation unit F as gaseous nitrogen is different from the invention embodied by FIG. 1.

Liquid nitrogen is fed from liquid nitrogen storage tank A through line 10 to a temperature control unit J, such as the Linde Cumulus™ FTC unit, where it will contact a heat transfer fluid in line 12. The heat transfer fluid will raise the temperature of the liquid nitrogen and cause it to enter the gaseous state where it will exit the temperature control unit J through line 11 and through open valve V2 will enter the ozone separation unit F.

The cooling loop will contact a thermal cooling jacket G1 surrounding the ozonation reactor G to keep the ozonation reactor at a sufficiently stable cold temperature. A booster blower or compressor K will assist in feeding the heat transfer fluid through line 12 in a loop with the thermal cooling jacket G1. An expansion tank 1 is present to assist in any coolant expansion and related pressure increase.

While this invention has been described with respect to particular embodiments thereof, it is apparent that numerous other forms and modifications of the invention will be obvious to those skilled in the art. The appended claims in this invention generally should be construed to cover all such obvious forms and modifications which are within the true spirit and scope of the invention.

Having thus described the invention, what we claim is:

1. A method for generating ozone for use in ozonolysis of organic compounds comprising the steps of:
   a) feeding liquid oxygen to a heat exchanger thereby forming gaseous oxygen;
   b) feeding gaseous oxygen to an ozone generator;
   c) feeding a mixture of ozone and oxygen to an ozone separation unit;
   d) feeding liquid nitrogen to a temperature control unit whereby said liquid nitrogen is heated and becomes gaseous;
   e) feeding said gaseous nitrogen to said ozone separation unit;
   f) feeding a mixture of ozone and nitrogen to an ozonation reactor; and
   g) transferring cooling from said temperature control unit to a cooling jacket surrounding said ozonation reactor.

2. The method as claimed in claim 1 wherein said organic compounds are selected from the group consisting of alkenes, alkynes, benzyl ethers, and oleic acid.

3. The method as claimed in claim 2 wherein said ozone separation unit is an oxygen to ozone pressure swing adsorption system.

4. The method as claimed in claim 3 wherein said pressure swing adsorption system contains an adsorbent selected from the group consisting of silica gel and high silica zeolites.

5. The method as claimed in claim 2 wherein said ozone separation unit is a membrane-based separation system.

6. The method as claimed in claim 1 further comprising feeding said gaseous nitrogen to said ozonation reactor.

7. The method as claimed in claim 1 wherein a compressor assists in feeding heat transfer fluid in a loop with said thermal cooling jacket.

8. The method as claimed in claim 1 further comprising an expansion tank to assist with coolant expansion.

\* \* \* \* \*